United States Patent [19]

Robertson et al.

[11] Patent Number: 5,053,221

[45] Date of Patent: Oct. 1, 1991

[54] NOVEL MASCARA COMPOSITION HAVING VERY SMALL PARTICLES

[75] Inventors: Sharon R. Robertson, Collierville; Robert J. Edmundson, Germantown, both of Tenn.

[73] Assignee: Maybe Holding Co., Wilmington, Del.

[21] Appl. No.: 439,967

[22] Filed: Nov. 20, 1989

[51] Int. Cl.$^5$ .............................................. A61K 7/021
[52] U.S. Cl. ........................................ 424/63; 424/78; 424/81; 424/401
[58] Field of Search ..................... 424/78, 63, 401, 81

[56] References Cited

U.S. PATENT DOCUMENTS

| | | | |
|---|---|---|---|
| 4,423,031 | 2/1983 | Murui et al. | 424/63 |
| 4,536,405 | 8/1985 | Nara et al. | 424/63 |
| 4,665,107 | 5/1987 | Micale | 523/105 |
| 4,801,445 | 1/1989 | Fukui et al. | 424/67 |
| 4,820,510 | 4/1989 | Arraudeau et al. | 424/63 |
| 4,906,458 | 3/1990 | Shigata et al. | 514/772 |

FOREIGN PATENT DOCUMENTS 1110240 4/1968 United Kingdom .
2191945 12/1987 United Kingdom .

*Primary Examiner*—Thurman K. Page
*Assistant Examiner*—P. Kulkosky
*Attorney, Agent, or Firm*—Sherman and Shalloway

[57] ABSTRACT

A novel mascara composition is disclosed. The composition comprises: (a) an effective amount of water; (b) an effective amount of microsphere particles selected from the group consisting of silica beads, polymethylmethacrylate beads, and combinations thereof; and (c) an effective amount of a water dispersible, high molecular weight, amorphous anionic polyester polymer having an approximate molecular weight, MN, of about 14,000 to about 16,000 and a melt viscosity at 200° C. of about 2000 to about 42,000 poise as measured with a Sieglaff-McKelvey Capillary Rheometer, 100 sec$^{-1}$ shear rate. The polyester polymer is added to the mascara composition as a water dispersion having a solids content of not more than about 40% by weight of the dispersion. Prepared mascara compositions contain silica beads polymethylmethacrylate beads and an effective amount of the emulsifier C12-C15 alcohols benzoate.

20 Claims, No Drawings

NOVEL MASCARA COMPOSITION HAVING VERY SMALL PARTICLES

BACKGROUND

There are many mascara formulations which are available to the consumer. These mascaras can contain ingredients—such as waxes, fibers, proteins or oils—which may eventually cause the mascara to flake. The flakes can be an inconvenience to the user because they may get on the user's face or build up on the user's contact lenses.

A mascara that contains no waxes nor fibers, gives a soft, long-lashed look, does not flake, and washed off with soap and water would be a welcome contribution to the art. This invention provides just such a contribution.

SUMMARY OF THE INVENTION

Surprisingly, we have discovered a mascara composition which: (1) does not require and therefore does not contain any waxes or fibers, and therefore avoids the problems of flaking; (2) is not heavy or goopy; (3) separates and lengthens lashes; (4) leaves lashes soft in appearance and to the touch; and (5) washes off with soap and water.

To achieve the highly desirable properties of the mascara compositions (formulations) of this invention two components are necessary: (1) tiny microspheres of silica or tiny microspheres of polymethylmethacrylate (hereinafter referred to as "PMMA") or combinations thereof; and (2) a water dispersable relatively high molecular weight amorphorous anionic polyester polymer which forms a clear film with a fast setting speed (e.g., about 60 to about 300 seconds).

Other known in the art ingredients useful for making mascara compositions may be blended with these two components to produce the desired end product. However, it is not necessary to add waxes or fibers to the compositions of this invention. Oils usually used in mascara compositions, such as hydrogenated fish oil, and proteins may also be left out of the compositions of this invention.

By using the above two components (silica and/or PMMA microspheres, and the dispersed anionic polymer) in combination with such optional known ingredients as emulsifiers, emollients, humectants, drying agents, preservatives, colorants, and pH adjusters, mascara compositions of this invention are obtained.

Thus, this invention provides a mascara composition comprising:

(a) an effective amount of water;

(b) an effective amount of microsphere particles selected from the group consisting of silica microspheres (beads), polymethylmethacrylate microspheres (beads), and combinations thereof; and (c) an effective amount of a water dispersable relatively high molecular weight amorphorous anionic polyester polymer, said polymer having an approximate molecular weight, Mn, of about 14,000 to about 16,000 (i.e., a molecular weight of about 14,000 to about 16,000 Mn) and a melt viscosity at 200° C. of about 2000 to about 42,000 poise as measured with a Sieglaff-McKelvey Capillary Rheometer, 100 sec$^{-1}$ shear rate.

This invention also provides a mascara composition comprising:

(a) an effective amount of water;

(b) an effective amount of microsphere particles selected from the group consisting of: silica microspheres (beads), polymethyl methacrylate microspheres (beads), and combinations thereof; and (c) an effective amount of a water dispersed relatively high molecular weight (suitably about 14,000 to about 16,000 Mn) amorphorous anionic polyester polymer having a melt viscosity at 200° C. of about 2000 to about 42,000 poise as measured with a Sieglaff-McKelvey Capillary Rheometer, 100 sec$^{-1}$ shear rate, wherein the dispersion comprises an amount of said polyester polymer which is effective to form a clear film when said mascara composition is applied to the eye lashes of the user.

In a preferred embodiment, this invention provides a mascara composition comprising:

(a) an effective amount of water;

(b) an effective amount of silica microspheres (beads);

(c) an effective amount of PMMA microspheres (beads); and (d) an effective amount of a water dispersed relatively high molecular weight amorphorous anionic polyester polymer, wherein the dispersion comprises an amount of said polyester polymer which is effective to form a clear film when said mascara composition is applied to the eye lashes of the user.

DETAILED DESCRIPTION OF THE INVENTION

The silica beads are used in amounts which are effective to provide increased surface area for a faster drying time and a smoother application. Generally, the silica beads are of a size which allows suitable blending of the silica beads into the mascara composition and which provides the desired surface area. Suitable silica beads have a particle size of about 1 to about 16 microns.

When the silica beads are used without the combined use of the PMMA beads (i.e., when the silica beads are the only microsphere particles), the silica beads are used in amounts of about 0.5 to about 11.5% by weight of the total composition, with about 2.5 to about 5.0% being preferred. When the silica beads are used in combination with the PMMA beads, the silica beads are used in amounts of about 0.5 to about 4.0% by weight of the total composition, with about 1.0 to about 2.0% being preferred.

The preferred silica beads are commercially available under the product designation SB-700 from U.S. Cosmetics Corporation, 328 Kennedy Drive, Putnam, Conn. 06260. The SB-700 silica beads are reported to be white spherical porous silica beads with a hole in the center having more than 99.0% $SiO_2$. The SB-700 silica beads are reported as having the specifications: (1) water soluble matter, less than 2%; (2) heavy metals, less than 20 ppm Pb, less than 3 ppm As, less than 1 ppm Hg; (3) loss on drying, less than 10% (due to the hygroscopic nature of this product, once the package is opened it is possible to go up to 15%); (4) loss on ignition, less than 15% (it is possible to go up to 20% after the package is opened due to the hygroscopicity of this product); (5) pH, 7–8.5; (6) specific volume, 1.8–2.4 ml/g; (7) specific surface area, 600–800 $M^2/g$; (8) oil absorption, 1.4–1.5 ml/g; (9) pore size 50–150 angstroms (5–15 millimicrons); and (10) total pore volume, 1.248 cc/g.

The PMMA beads are used in amounts which are effective to provide increased surface area for a faster drying time and a smoother application. Generally, the PMMA beads are of a size which allows suitable blending of the PMMA beads into the mascara composition and which provides the desired surface area. Suitable PMMA beads have a particle size of about 1 to about 24 microns.

When the PMMA beads are used without the combined use of silica beads (i.e., when the PMMA beads are the only microsphere particles), the PMMA beads are used in amounts of about 0.5 to about 11.5% by weight of the total composition, with about 2.5 to about 5.0% being preferred. When the PMMA beads are used in combination with the silica beads, the PMMA beads are used in amounts of about 0.5 to about 7.5% by weight of the total composition, with about 2.5 to about 5.0% being preferred.

The preferred PMMA beads are commercially available under the product designation Techpolymer MB-8C from U.S. Cosmetics Corporation, Putnam, Conn. The MB-8C PMMA beads are reported as having the specifications: (1) particle size, 1 to 24 microns with an average of 6.6 microns; (2) particle shape, spherical; (3) melting point, 100° C.; (4) specific gravity, 1.15 to 1.25; (5) loss on drying, less than 1%; (6) lead, less than 10 ppm; (7) arsenic, less than 1 ppm; and (8) methylmethacrylate monomer, not detected.

Preferably, the mascara compositions of this invention contain the PMMA beads and the silica beads.

Most preferably, the mascara compositions of this invention contain the silica beads, the PMMA beads having the characteristics described above for the Techpolymer MB-8C PMMA beads, and an effective amount of the emulsifier C12-C15 alcohols benzoate. Usually, the C12-C15 alcohols benzoate is present in an amount of about 1 to about 10% by weight of the total composition. The C12-C15 alcohols benzoate is well known to those skilled in the art—see, for example, the CTFA Cosmetic Ingredient Handbook cited below. It has surprisingly been discovered that this particular emulsifier in combination with the PMMA beads having the characteristics of the Techpolymer MB-8C PMMA beads results in a gel which produces a highly desirable film that is believed to have the PMMA beads arranged in a monolayer.

The mascara compositions of this invention contain a water dispersable polyester polymer which has a fast setting speed (e.g., about 60 to about 300 seconds)—i.e., a fast drying time—and which forms a hard, clear, flexible film that adheres gently to the lashes. The polyester polymer used also has the characteristic of being removable with soap and water.

The water dispersable polyester polymer is used in an amount which is effective to provide a hard, clear, flexible film that adheres to the lashes. The mascara compositions of this invention contain the water dispersable polyester polymer in amounts of about 1.0 to about 3.0% by weight of the total composition with about 1.5 to about 2.5% being preferred. These amounts of solid polymer are usually dispersed in water before being added to the mascara compositions.

The dispersions of the polyester polymer are usually added to the mascara compositions in amounts of about 3.5 to about 10.0% by weight of the total composition with about 5.0 to about 7.5% being preferred. The dispersions contain sufficient polyester polymer to have a solids content that, when the dispersions are added in the amounts specified, results in the mascara compositions having the amounts of solid polymer specified. Generally, the dispersions will not have a solids content that is more than about 40% by weight of the dispersion. Usually the dispersions will have a solids content that is of about 20 to about 40% by weight of the dispersion, with about 28 to about 36% being preferred, and about 30 to about 36% being most preferred. Although dispersions having a solids content that is less than 20% by weight of the dispersion can be made (e.g. 1% to 20%), they are not convenient to use because of the large quantity of dispersion that would have to be added to the mascara compositions to obtain the desired level of polyester polymer. The dispersions can be made by techniques known to those skilled in the art or obtained from a commercial supplier as discussed below. Those skilled in the art will also appreciate that when the dispersions are made care is to be taken to avoid microbiological contamination (e.g., yeast contamination).

The preferred polymers are available from Eastman Chemicals under the general product designation EASTMAN AQ polymers. These polymers are reportedly relatively high molecular weight, amorphous polyesters that disperse directly in water without the assistance of organic cosolvents, surfactants, or amines. It is reported that this water-dispersibility is attributable, in large part, to the presence of ionic substituents attached to the polymer chain—see Formula I below. It is also reported that some of the aromatic dicarboxylic acid units in EASTMAN AQ polymer chains have sodiosulfo (SO$_3$−Na+) substituents; although only two are shown in Formula I below, on the average, there are five to eight ionic sodiosulfo substituents per molecule.

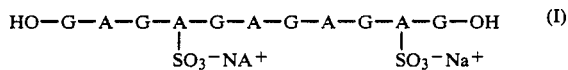
(I)

In Formula I, A is an aromatic dicarboxylic acid moiety, G is an aliphatic or cycloaliphatic glycol residue, and —OH are hydroxy end groups.

Suitable polyester polymers are commercially available under the product designations AQ29S, AQ38S, AQ55S, AQ29D, AQ38D, and AQ55D from Eastman Chemical Products, Inc. The polymers may be obtained in the solid form (indicated by the letter "S" in the product designation) or the dispersed form (indicated by the letter "D" in the product designation). If obtained in the solid form, the polymer dispersions can be made as discussed below. It has been found that while the AQ29D gives satisfactory results, it may not give what might be considered an optimum commercial product.

AQ29S is reported to have the specifications: (1) approximate molecular weight, Mn, 16,000; (2) hydroxyl number, <10; (3) acid number, <2; (4) Tg, °C., 29; and (5) melt viscosity at 200° C. (392° F.), 2000 poise, as measured with a Sieglaff-McKelvey Capillary Rheometer, 100 sec$^{-1}$ shear rate.

AQ38S is reported to have the specifications: (1) approximate molecular weight, Mn, 14,000; (2) hydroxyl number, <10; (3) acid number, <2; (4) Tg, °C., 38; (5) melt viscosity at 200° C. (392° F.), 9700 poise, as measured with a Sieglaff-McKelvey Capillary Rheometer, 100 sec$^{-1}$ shear rate.

AQ55S is reported to have the specifications: (1) approximate molecular weight, Mn, 14,000; (2) hydroxyl number, <10; (3) acid number, <2; (4) Tg, °C., 55; (5) melt viscosity at 200° C. (392° F.), 42,000 poise, as measured with a Sieglaff-McKelvey Capillary Rheometer, 100 sec$^{-1}$ shear rate.

AQ29D is reported to have the specifications: (1) percent solids (in water), 30; (2) ionic type, anionic; (3) pH, 5-6; (4) viscosity, 45 cP (centipoise) at 100 rpm as measured with a Brookfield Viscometer, Model RVT, Spindle No. 1, 23° C. (74° F.); (5) density at 24° C. (75° F.), 1.06 g/mL; and (6) chemical oxygen demand (COD), 1630 mg/g solids.

AQ38D is reported to have the same specifications as AQ29D except: percent solids, 25; viscosity, 30 cP; and COD, 1700 mg/g solids.

AQ55D is reported to have the same specifications as AQ29D except: percent solids, 28; viscosity, 42 cP; density, 1.08 g/mL; and COD, 1750 mg/g solids.

These polymers are believed to have structural units of diglycol-cyclohexanedimethanol-isophthalates-sulfoisophthalates. Dispersions having different percent solids (than those stated above for AQ29D, AQ38D and AQ55D) may be obtained from Kodak Chemical Products, Inc.

A dispersion of AQ55S having a solids content (as measured with 1 g of dispersion at 105° C. for 1 hour) of about 30 to about 36% by weight of the dispersion and a pH of 5.6 to 6.6 is preferred.

Preparation of a dispersion of Eastman AQ polymers may be exemplified in the preparation of 190 liters (50 U.S. gallons) of 30% solids polymer dispersed in water. In Step 1, 133 liters (35 U.S. gallons) of soft water (less than 20 ppm total hardness) is placed in a tank or vessel equipped with an agitator. The tank drain should be covered with a screen to prevent pellets from entering the drain pipe. The water should be heated to and maintained in the temperature ranges shown below as pellets of the appropriate polymer are added.

(a) AQ29S 75°-85° C. (167°-185° F.)
(b) AQ38S 90°-95° C. (194°-203° C.)
(c) AQ55S 85°-90° C. (185°-194° F.)

In Step 2, the agitator is started and 57 Kg (125 pounds) of polymer pellets are slowly sifted into the water. If the pellets are added to quickly, lumping may occur. The rate of agitation should be sufficient to maintain the pellets in suspension. In Step 3, heating is continued in the appropriate temperature range with good agitation until all the pellets are dispersed (usually 20 to 30 minutes). Water is added as needed to replace evaporation loss. In Step 4, the dispersion is cooled below 40° C. (104° F.). In Step 5, the dispersion is filtered before use.

Those skilled in the art will appreciate that dispersions having other percent solids may be obtained in various amounts by a suitable modification of the above described process. Such modifications are well within the capabilities of those skilled in the art without the need for undue experimentation.

Further information about the Eastman AQ polymers may be obtained from the Eastman Chemicals product brochure titled, "EASTMAN AQ® POLYMERS Properties and Applications", Publication No. GN-389, March 1989, the disclosure of which is incorporated herein by reference thereto.

Usually, the polyester polymer, and the silica beads and/or PMMA beads are combined with effective amounts of other ingredients known to those skilled in the art as being useful in mascara compositions. These other ingredients are selected from the group consisting of: (1) water, as a moisturizing agent, usually used in amounts of about 30 to about 70% by weight; (2) drying agents, such as SD alcohol 40, kaolin, talc, silica, silk powder and the like, usually used in amounts of about 1 to about 15% by weight; (3) emulsifiers (emulsifying agents), such as methyl glucose sesquistearate, cetearyl alcohol (a mixture of fatty alcohols consisting predominantly of cetyl and stearyl alcohols), ceteareth-10 (the polyethylene glycol ether of cetearyl alcohol that conforms generally to the formula $R(OCH_2CH_2)_nOH$ wherein R represents a blend of cetyl and stearyl radicals and n has an average value of 10), methyl gluceth-20 sesquistearate (a mixture of mono and diesters of methyl gluceth-20 and stearic acid, wherein methyl gluceth-20 is the polyethylene glycol ether of methyl glucose that conforms generally to the formula $CH_3—C_6H_{10}O_5—(OCH_2CH_2)_nOH$, wherein n has an average value of 20), pentaerythritol tetrabehenate and the like, usually used in amounts of about 1 to about 10% by weight; (4) emollients, such as C12-C15 alcohols benzoate, panthenol and the like, usually used in amounts of about 1 to about 10% by weight; (5) humectants, such as propylene glycol, hydrolyzed silk, silk amino acids and the like, usually used in amount of about 1 to about 3% by weight; (6) thickeners (viscosity control agents), such as hydroxyethyl cellulose and the like, usually used in amounts of about 0.2 to about 0.5% by weight; (7) preservatives, such as imidazolidinyl urea, methylparaben, propylparaben and the like, usually used in amounts of about 0.05 to about 1.0% by weight; (8) colorants (coloring agents), such as iron oxides, ultramarine blue and the like, usually used in amounts of about 0.50 to about 20% by weight; and (10) pH adjusters, such as sodium hydroxide, triethanolamine and the like, usually used in amounts of about 0.05 to about 1.0% by weight; wherein all percents are percent by weight of the total composition. Those skilled in the art will appreciate that the sum total of all ingredients used in the mascara compositions of this invention is equal to 100% by weight.

These ingredients are well known to those skilled in the art, for example see Nikitakis, J. M., editor, *CTFA Cosmetic Ingredient Handbook*, First Edition, published by The Cosmetic, Toiletry and Fragrance Association, Inc., 1110 Vermont Avenue, N.W. Washington, D.C. 20005, copyright 1988, the disclosure of which is incorporated herein by reference thereto. Those skilled in the art will appreciate that other ingredients may be used for their known intended use in the mascara compositions of this invention, and such ingredients may be selected from those known in the art in accordance with the teachings herein, and such selection may be made without the need for undue experimentation.

While it is anticipated that other suitable ingredients known in the art and falling within the above described categories (e.g., emollients, emulsifiers, humectants, etc.) may prove useful, it has been discovered that certain ingredients do not, at the amounts tested, result in a satisfactory end product. The ingredients which did not provide a satisfactory final product at the % by weight indicated in parentheses were:

Guar C26IN (guar hydroxypropyl trimonium chloride, 0.25); Guar FG-1 (guar gum, 0.25); Keltrol T (xanthan gum, 0.25); CMC (cellulose gum, 0.25); Water lock A100 (hydrolyzed starch-acrylonitrile graft copolymer salts, 0.25, 0.50); Bayberry #1641 (fish glyceride and bayberry wax, 2.00); Beeswax SP453 (white beeswax, 2.00, 2.10, 3.00, 4.00); Candelilla wax (1.00); Carnauba #63 (carnauba, 2.00, 3.00, 310); DC 200/350 (dimethicone, 4.50); DC 345 (cyclomethicone, 4.50); Generol 122 (soya sterol, 3.00); Generol 122E25 (PEG-25 soya sterol, 5.00); Hostacerin WO (polyglyceryl-2 sesquiisostearate and beeswax and mineral oil and magnesium stearate and aluminum stearate, 2.50); Pationic ISL (sodium isostearoyl lactylate, 3.00, 5.00); Pelemol ISB (isostearyl behenate, 1.00, 1.50, 2.50); Syntran 5170 (ammonium acrylates copolymer and propylene glycol and potassium octoxynol-12 phosphate and sodium lauryl sulfate and nonoxynol-10, 10.00); Carboset XL28 (acrylic/acrylate copolymer and quaternium-15, 2.00); Ohlan (hydroxylated lanolin, 1.00); Ganex V216 (alkylated vinylpyrrolidone PVP/hexadecene copolymer, 2.00, 4.50); PVP K30 (polyvinylpyrrolidone K30, 1.50, 3.00); PEAC 617G (polyethylene, 2.00, 5.00); Indopol H100 (polybutene, 2.50, 3.00, 4.00, 5.00); Pecogel H12 (PVP/urethane hydrogel, 5.00); Neocryl (styrene/acrylate/acrylonitrile copolymer, 5.00); and Chitin Liquid HV (carboxymethyl chitin, 5.00).

A typical composition of this invention contains the polyester polymer, silica beads and/or PMMA beads (as discussed above), water as a moisturizer, emollients, emulsifiers, and humectants. These ingredients are usually blended together in accordance with the procedure set forth in Example 1 below. A critical aspect of producing the compositions of this invention is the need to apply enough sheer, such as by milling, in processing from the dispersing of the colorant in the water phase, through the emulsification of the product, down to 50° C. where the composition begins to thicken in order to attain the desired micelle size and viscosity, e.g., >125,000 cp. Other known in the art mascaras are not as sensitive to this need for adequate milling time in order to achieve the desired micelle size, desired finished product viscosity and/or appearance in the finished composition (product).

The following examples are illustrative only and should not be construed as limiting the invention in any way. Those skilled in the art will appreciate that variations are possible which are within the spirit and scope of the appended claims.

The ingredients listed by their product designations or tradenames in the examples that follow are identified:

(1) Natrosol 250 HHR (from Aqualon): hydroxyethylcellulose;

(2) Glucamate SSE-20 (from Amerchol): methyl gluceth-20 sesquistearate;

(3) Finsolv TN (from Finetex): C12–C15 alcohols benzoate;

(4) Phoenoxol J (from Phoenix): cetearyl alcohol and ceteareth-10;

(5) Glucate SS (from Amerchol): methyl glucose sesquistearate;

(6) Liponate PB-4 (from Lipo): pentaerythritol tetrabehenate;

(7) Kaolin 270 (from FR Hall): China Clay NF (8) D-Panthenol 50P (from BASF): panthenol and propylene glycol;

(9) Crosilk Liquid (from Croda): silk amino acids;

(10) Crosilk 10,000 (from Croda): hydrolyzed silk protein;

(11) Silk Powder (from Croda): silk powder;

(12) Germal 115 (from Sutton): imidazolidinyl urea; and

(13) SD Alcohol 40 (from Union Carbide): ethyl alcohol denatured with brucine sulfate and tertiary butyl alcohol, 190 proof.

EXAMPLE 1

A blue mascara composition of this invention was produced by blending together the ingredients listed in Table 1.

TABLE 1

| BLUE MASCARA COMPOSITION | |
|---|---|
| Ingredient | % By Weight |
| Part A | |
| Water | 43.149 |
| Natrosol 250 HHR | 0.40 |
| Methylparaben, USP | 0.25 |
| AQ 55 D (33% solids) | 5.00 |
| Glucamate SSE-20 | 2.10 |
| Part B | |
| Black, Iron oxide 7133 | 1.60 |
| Blue, ultramarine 7104 | 6.40 |
| Kaolin 270 | 5.00 |
| SB 700 (silica beads) | 1.00 |
| Part C | |
| Finsolv TN | 2.50 |
| PMMA beads (Techpolymer MB-8C) | 2.50 |
| Phoenoxol J | 3.50 |
| Glucate SS | 4.90 |
| Liponate PB-4 | 1.00 |
| Propylparaben, USP | 0.10 |
| Part D | |
| Water | 5.00 |
| Part E | |
| Propylene Glycol, USP | 1.50 |
| D-Panthenol 50P | 0.20 |
| Crosilk Liquid | 0.25 |
| Crosilk 10,000 | 0.25 |
| Silk Powder | 0.15 |
| Part F | |
| Water | 1.00 |
| Germall 115 | 0.25 |
| Part G | |
| SD Alcohol 40 | 10.00 |
| Part H | |
| Sodium Hydroxide (10% Solution) | 0.001 |

The ingredients in Table 1 were blended together by the following procedure. The water from Part A was added to a suitable mixing vessel equipped with means for providing suitable agitation (i.e. a steam jacketed kettle equipped with a lightnin mixer or other suitable agitation). The AQ 55 D polymer was added to the water and mixed until homogeneous using sufficient agitation to form a vortex. Thereafter, the Natrosol 250 HHR was slowly sprinkled in so that it did not lump. After the Natrosol 250 HHR was added, the agitation was slowed down to avoid air entrapment. Heating of this mixture to 70°–75° C. (158°–168° F.) was begun. The mixing vessel was covered as much as possible to avoid any evaporation loss.

While the mixture was heated to 70°–75° C., the remaining ingredients of Part A were added and the entire mixture was mixed until uniform and the temperature was maintained. The resulting mixture was transferred to a steam jacketed kettle equipped with double motion agitation.

Next, the ingredients of Part B were added to the mixture and the resulting mixture was mixed until the pigments were wetted out. The mixture was recirculated through a colloid mill at a low gap setting of 1–5 for about 30 minutes while the temperature was maintained at 70°–75° C.

The ingredients of Part C were added to another steam jacketed kettle equipped with suitable agitation and they were mixed and heated to 70°–75° C.

With both phases (oil and water) at 70°–75° C., Part C was added to the mixture (Parts A and B). The resulting mixture was mixed until uniform and the temperature was maintained. The mixture was recirculated through the colloid mill at 20–30 gap. Forced cooling of the mixture to 45°–50° C. (113°–122° F.) was begun while continuing to recirculate the mixture through the mill.

Recirculation was discontinued when the temperature of the mixture was below 50° C. The rinse water of Part D was added through the mill and into the mixture.

Next, the Part E ingredients were premixed together, and then the premixed Part E was added to the mixture and the resulting mixture was mixed until uniform.

Next, the Part F ingredients were premixed together, and then premixed Part F was added to the mixture. The resulting mixture was mixed until uniform. Forced cooling to 40°–45° C. was continued.

When the temperature of the mixture reached 40°–45° C. the alcohol of Part G was slowly added to the mixture. The resulting mixture was mixed with sufficient agitation to incorporate the alcohol without aeration. The mixture was mixed until uniform, and the lid to the mixing vessel was kept closed as much as possible to avoid any evaporation loss.

Forced cooling of the mixture was continued until room temperature was reached.

The pH was adjusted, as necessary, with the sodium hydroxide (pH adjuster) of Part H until the pH was 7.5 to 7.8. The finished mixture can be stored in polyethylene bag lined metal containers or HDPE plastic buckets until ready for use.

EXAMPLE 2

A black mascara composition of this invention was produced by blending together the ingredients listed in Table 2. The procedure of Example 1 was followed except no pH adjustment with sodium hydroxide was needed.

TABLE 2

| BLACK MASCARA COMPOSITION | |
|---|---|
| Ingredient | % By Weight |
| Part A | |
| Water | 43.15 |
| Natrosol 250 HHR | 0.40 |
| Methylparaben, USP | 0.25 |
| AQ 55 D (33% solids) | 5.00 |
| Glucamate SSE-20 | 2.10 |
| Part B | |
| Black, Iron oxide 7133 | 8.00 |
| Kaolin 270 | 5.00 |
| Talc 1615 | 2.00 |
| SB 700 (silica beads) | 1.00 |
| Part C | |
| Phoenoxol J | 3.50 |
| Glucate SS | 4.90 |
| Liponate PB-4 | 1.00 |
| Finsolv TN | 2.50 |
| PMMA beads (Techpolymer MB-8C) | 2.50 |
| Propylparaben, USP | 0.10 |
| Part D | |
| Water | 5.00 |
| Part E | |
| Propylene Glycol | 1.50 |
| D-Panthenol 50P | 0.20 |
| Crosilk Liquid | 0.25 |
| Crosilk 10,000 | 0.25 |
| Silk Powder | 0.15 |
| Part F | |
| Water | 1.00 |
| Germall 115 | 0.25 |
| Part G | |

TABLE 2-continued

| BLACK MASCARA COMPOSITION | |
|---|---|
| Ingredient | % By Weight |
| SD Alcohol 40 | 10.00 |

EXAMPLE 3

A brown mascara composition of this invention was produced by blending together the ingredients listed in Table 3. The procedure of Example 1 was followed except no pH adjustment with sodium hydroxide was needed.

TABLE 3

| BROWN MASCARA COMPOSITION | |
|---|---|
| Ingredient | % By Weight |
| Part A | |
| Water | 43.15 |
| Natrosol 250 HHR | 0.40 |
| Methylparaben, USP | 0.25 |
| AQ 55 D (33% solids) | 5.00 |
| Glucamate SSE-20 | 2.10 |
| Part B | |
| Black, Iron oxide (Black) 7133 | 6.21 |
| Red, Iron oxide (Red) 8075 | 0.59 |
| Yellow, Iron oxide (Yellow) 7055 | 1.20 |
| Kaolin 270 | 5.00 |
| Talc 1615 | 2.00 |
| SB 700 (silica beads) | 1.00 |
| Part C | |
| Finsolv TN | 2.50 |
| PMMA beads (techpolymer MB-8C) | 2.50 |
| Phoenoxol J | 3.50 |
| Glucate SS | 4.90 |
| Liponate PB-4 | 1.00 |
| Propylparaben, USP | 0.10 |
| Part D | |
| Water | 5.00 |
| Part E | |
| Propylene Glycol | 1.50 |
| D-Panthenol 50P | 0.20 |
| Crosilk Liquid | 0.25 |
| Crosilk 10,000 | 0.25 |
| Silk Powder | 0.15 |
| Part F | |
| Water | 1.00 |
| Germall 115 | 0.25 |
| Part G | |
| SD Alcohol 40 | 10.00 |

Those skilled in the art will appreciate that the total amount of all ingredients (components) used in the composition of this invention equals 100% by weight of the total composition. Also, unless stated otherwise all percents and amounts are percent by weight of the total composition.

The invention being thus described, it will be obvious that the same may be varied in many ways. Such variations are not to be regarded as a departure from the spirit and scope of the invention and all such modifications are intended to be included within the scope of the claims.

What is claimed is:

1. A non-flaking, soapy water removable mascara composition comprising:
   (a) 30–70% by weight of water;
   (b) 0.05–11% by weight of microsphere particles selected from the group consisting of silica beads, polymethylmethacrylate beads, and combinations thereof; and (c) 1.0-3.0% by weight of a clear film-forming high molecular weight amorphous anionic polyester polymer represented by Formula 1:

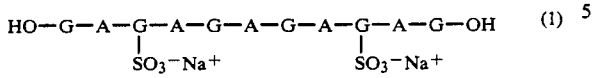

wherein A is an aromatic dicarboxylic acid moiety, G is a residue selected from the group consisting of an aliphatic residue and a cycloaliphatic glycol residue, —OH are hydroxy end groups, and the polymer chains have an average of five to eight ionic $SO_3^-Na^+$ substituents per molecule, and said polymer has an approximate molecular weight Mn of about 14,000 to about 16,000 and a melt viscosity at 200° C. of about 2000 to about 42,000 poise as measured with a Seiglaff-McKelvey Capillary Rheometer, 100 $sec^{-1}$ shear rate; said composition further comprising an effective amount of at least one other cosmetically acceptable mascara ingredient selected from the group consisting of drying agents, emulsifiers, emollients, humectants, thickeners, preservatives, colorants, and pH adjusters.

2. The composition of claim 1 wherein said polyester polymer contains molecules of diglycol-cyclohexanedimethanol-isophthalates-sulfoisophthalates.

3. The composition of claim 2 wherein said polymer is selected from the group consisting of:
   (a) a polymer having the specifications:
     (i) approximate molecular weight, Mn, 16,000;
     (ii) hydroxyl number, <10;
     (iii) acid number, <2;
     (iv) Tg, °C., 29; and
     (v) melt viscosity at 200° C., 2000 poise;
   (b) a polymer having the specifications:
     (i) approximate molecular weight, Mn, 14,000;
     (ii) hydroxyl number, <10;
     (iii) acid number, <2;
     (iv) Tg, °C., 38; and
     (v) melt viscosity at 200° C., 9700 poise; and
   (c) a polymer having the specifications;
     (i) approximate molecular weight, Mn, 14,000;
     (ii) hydroxyl number, <10;
     (iii) acid number, <2;
     (iv) Tg, °C., 55; and
     (v) melt viscosity at 200° C., 42,000 poise.

4. The composition of claim 3 wherein said polymer is (c).

5. The composition of claim 4 wherein said composition contains silica beads and polymethylmethacrylate beads.

6. The composition of claim 5 wherein there is additionally added to said composition 1-10% by weight of C12-C15 alcohols benzoate, and said polymethylmethacrylate beads have a particle size of 1 to 24 microns, a melting point of 100° C., and a specific gravity of about 1.15 to about 1.25.

7. The composition of claim 1 wherein said microsphere particles are polymethylmethacrylate beads.

8. The composition of claim 7 where there is additionally added to said composition 1-10% by weight of C12-C15 alcohols benzoate, and said polymethylmethacrylate beads have a particle size of 1 to 24 microns, a melting point of 100° C., and a specific gravity of 1.15 to 1.25.

9. The composition of claim 1 wherein there is added to said composition an effective amount of at least one other cosmetically acceptable ingredient selected from the group consisting of:
   (a) drying agents selected from the group consisting of: SD alcohol 40, kaolin, talc, silica, and silk powder;
   (b) emulsifiers selected from the group consisting of: methyl glucose sesquistearate, cetearyl alcohol, ceteareth-10, methyl gluceth-20 sesquistearate, and pentaerythritol tetrabehenate;
   (c) emollients selected from the group consisting of: C12-C15 alcohols benzoate, and panthenol;
   (d) humectants selected from the group consisting of: propylene glycol, hydrolyzed silk, and silk amino acids;
   (e) hydroxyethyl cellulose as a thickener;
   (f) preservatives selected from the group consisting of: imidazolidinyl urea, methylparaben, and propylparaben;
   (g) colorants selected from the group consisting of: iron oxides, and ultramarine blue; and
   (h) pH adjusters selected from the group consisting of: sodium hydroxide and triethanolamine.

10. A non-flaking, soapy water removable mascara composition comprising:
   (a) 30-70% by weight of water;
   (b) 0.05-11% by weight of microsphere particles selected from the group consisting of silica beads, polymethylmethacrylate beads, and combinations thereof; and
   (c) 3.5-10.0% of a water dispersed high molecular weight amorphous anionic polyester polymer, said dispersed polyester polymer having a solids content that is not more than about 40% by weight of the dispersion, represented by Formula 1:

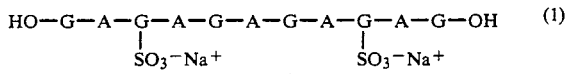

wherein A is an aromatic dicarboxylic acid moiety, G is a residue selected from the group consisting of an aliphatic residue and a cycloaliphatic glycol residue, —OH are hydroxy end groups, and the polymer chains have an average of five to eight ionic $SO_3^-Na^+$ substituents per molecule, and said polymer has an approximate molecular weight Mn of about 14,000 to about 16,000 and a melt viscosity at 200° C. of about 2000 to about 42,000 poise as measured with a Seiglaff-McKelvey Capillary Rheometer, 100 $sec^{-1}$ shear rate, and wherein the dispersion comprises an amount of said polymer which is effective to form a clear film when said mascara composition is applied to the eyelashes of the user;
said composition further comprising an effective amount of at least one other cosmetically acceptable mascara ingredient selected from the group consisting of drying agents, emulsifiers, emollients, humectants, thickeners, preservatives, colorants, and pH adjusters.

11. The composition of claim 10 wherein said polyester polymer contains molecules of diglycol-cyclohexanedimethanol-isophthalates-sulfoisophthalates.

12. The composition of claim 11 wherein said polymer is selected from the group consisting of:
   (a) a polymer having the specifications:
     (i) approximate molecular weight, Mn, 16,000;
     (ii) hydroxyl number, <10;
     (iii) acid number, <2;

(iv) Tg, °C., 29; and
(v) melt viscosity at 200° C., 2000 poise;
(b) a polymer having the specifications;
(i) approximate molecular weight, Mn, 14,000;
(ii) hydroxyl number, <10;
(iii) acid number, <2;
(iv) Tg, °C., 38; and
(v) melt viscosity at 200° C., 9700 poise; and
(c) a polymer having the specifications;
(i) approximate molecular weight, Mn, 14,000;
(ii) hydroxyl number, <10;
(iii) acid number, <2;
(iv) Tg, °C., 55; and
(v) melt viscosity at 200° C., 42,000 poise.

13. The composition of claim 12 wherein said polymer is (c).

14. The composition of claim 13 wherein the dispersion has a solids content in water of about 28 to about 36% by weight of the dispersion.

15. The composition of claim 13 wherein the dispersion has a solids content in water of about 30 to about 36% by weight of the dispersion.

16. The composition of claim 15 wherein said composition contains silica beads and polymethylmethacrylate beads.

17. The composition of claim 16 wherein there is additionally added to said composition 1-10% by weight of C12-C15 alcohols benzoate, and said polymethylmethacrylate beads have a particle size of 1 to 24 microns, a melting point of 100° C., and a specific gravity of 1.15 to 1.25.

18. The composition of claim 10 wherein said microsphere particles are polymethylmethacrylate beads.

19. The composition of claim 18 wherein there is additionally added to said composition 1-10% by weight of C12-C15 alcohols benzoate, and said polymethylmethacrylate beads have a particle size of 1 to 24 microns, a melting point of 100° C., and a specific gravity of 1.15 to 1.25.

20. The composition of claim 10 wherein there is added to said composition an effective amount of at least one other cosmetically acceptable ingredient selected from the group consisting of:
(a) drying agents selected from the group consisting of: SD alcohol 40, kaolin, talc, silica, and silk powder;
(b) emulsifiers selected from the group consisting of: methyl glucose sesquistearate, cetearyl alcohol, ceteareth-10, methyl gluceth-20 sesquistearate, and pentaerythritol tetrabehenate;
(c) emollients selected from the group consisting of: C12-C15 alcohols benzoate, and panthenol;
(d) humectants selected from the group consisting of: propylene glycol, hydrolyzed silk, and silk amino acids;
(e) hydroxyethyl cellulose as a thickener.
(f) preservatives selected from the group consisting of: imidazolidinyl urea, methylparaben, and propylparaben;
(g) colorants selected from the group consisting of: iron oxides, and ultramarine blue; and
(h) pH adjusters selected from the group consisting of: sodium hydroxide and triethanolamine.

* * * * *

UNITED STATES PATENT AND TRADEMARK OFFICE
CERTIFICATE OF CORRECTION

PATENT NO. : 5,053,221
DATED : October 1, 1991
INVENTOR(S) :
Sharon R. Robertson and Robert J. Edmundson It is certified that error appears in the above-indentified patent and that said Letters Patent is hereby corrected as shown below:

Please change formula (I) at column 4, lines 33-37 to the following:

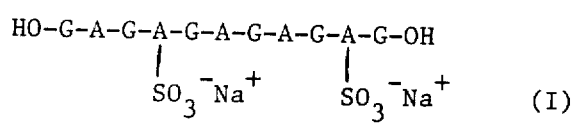

Please change formula (I) at column 11, lines 5-8 (in claim 1) and formula (I) at column 12, lines 35-39 (in claim 10) to the following:

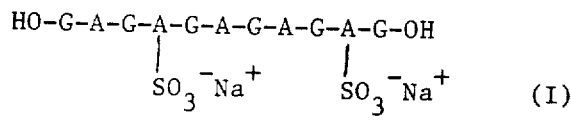

Signed and Sealed this

Twelfth Day of July, 1994

BRUCE LEHMAN

Attest:

Attesting Officer

Commissioner of Patents and Trademarks